United States Patent
Bosch i Lladó et al.

(10) Patent No.: US 7,265,223 B2
(45) Date of Patent: Sep. 4, 2007

(54) INTERMEDIATE COMPOUNDS FOR THE PREPARATION OF MIRTAZAPINE AND PRODUCTION METHODS THEREOF

(75) Inventors: Jordi Bosch i Lladó, Girona (ES);
Pelayo Camps García, Barcelona (ES);
Juan Contreras Lascorz, Celrà (ES);
Ma Carmen Onrubia Miguel, Barcelona (ES)

(73) Assignee: Medichem, S.A., Barcelona (ES)

( * ) Notice: Subject to any disclaimer, the term of this patent is extended or adjusted under 35 U.S.C. 154(b) by 368 days.

(21) Appl. No.: 10/488,909

(22) PCT Filed: Sep. 14, 2001

(86) PCT No.: PCT/ES01/00347

§ 371 (c)(1),
(2), (4) Date: Mar. 4, 2004

(87) PCT Pub. No.: WO03/024918

PCT Pub. Date: Mar. 27, 2003

(65) Prior Publication Data

US 2004/0236107 A1    Nov. 25, 2004

(51) Int. Cl.
C07D 241/04    (2006.01)
C07C 237/30    (2006.01)

(52) U.S. Cl. ..................... 544/403; 564/155
(58) Field of Classification Search ............ 544/403; 564/155
See application file for complete search history.

(56) References Cited

U.S. PATENT DOCUMENTS 3,102,068 A * 8/1963 Tolbert ............... 525/195
5,378,729 A * 1/1995 Kohn et al. ........... 514/231.2
5,681,962 A    10/1997 Callander

FOREIGN PATENT DOCUMENTS

FR    2585702    7/1985
WO    WO 00/63185    10/2000

OTHER PUBLICATIONS

Van Der Burg, W.J., *J. Med. Chem*, vol. 132, No. 1 (1970) pp. 35-39.

* cited by examiner

*Primary Examiner*—Emily Bernhardt
(74) *Attorney, Agent, or Firm*—Scully, Scott, Murphy & Presser P.C.

(57) ABSTRACT

The present invention is directed to intermediate compounds of mirtazapine and methods for obtaining same. A method is described for obtaining (±)-3-phenyl-1-methylpiperazine, an important intermediate for obtaining mirtazapine, which is based on imposing a cyclization reaction, in the presence of a reducing agent, on new compounds of general formula (1)

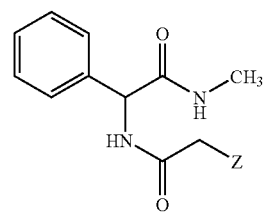

(I)

in which Z is a leaving group capable of undergoing a nucleophilic displacement. A method is also described for obtaining the new compounds of formula (1).

13 Claims, No Drawings

INTERMEDIATE COMPOUNDS FOR THE PREPARATION OF MIRTAZAPINE AND PRODUCTION METHODS THEREOF

FIELD OF THE INVENTION

This invention relates to a method for obtaining intermediate compounds useful in the preparation of the pharmaceutical active ingredient mirtazapine, as well as new intermediate compounds for said purpose.

STATE OF THE ART

Mirtazapine is the international common denomination (ICD) of compound 1,2,3,4,10,14b-hexahydro-2-methylpirazino[2,1-a]pyrido[2,3-c][2]benzazepine, of formula

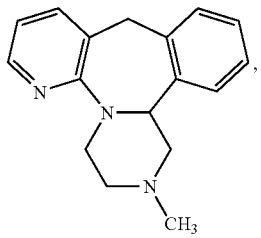

which is an antidepressive active ingredient first described in German patent application No. 2.614.406, published in 1976.

An important synthesis intermediate for the preparation of mirtazapine, which contributes structurally to a large part of the molecule thereof, is compound (±)-3-phenyl-1-methylpiperazine, of formula

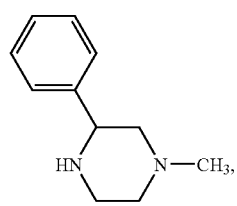

whereby an industrially advantageous production of said intermediate compound greatly conditions the industrial efficiency and costs of the preparation of the actual mirtazapine.

Example 4 of U.S. Pat. No. 4,772,705 describes a method for obtaining (±)-3-phenyl-1-methylpiperazine, which is summarised in the reaction sequence indicated in the following diagram.

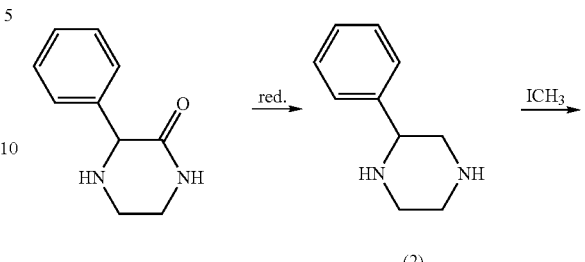

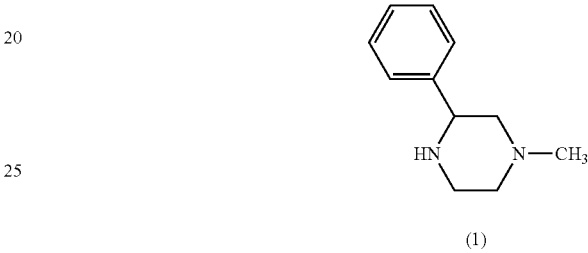

Thus, the derivative of oxo-piperazine (3) is reduced with aluminum and lithium hydride (LiAlH$_4$), in ethylic ether for 20 hours, to give the reduced compound (2) which, subsequently, undergoes methylation with methyl iodine (ICH$_3$) highly dissolved in acetone so that, after additional processing, the (±)-3-phenyl-1-methylpiperazine (1) is isolated in the form of the dihydrochloride thereof.

The starting compound (3) can be obtained, in turn, from phenylacetic acid, through bromation and esterification thereof until the ethyl α-bromophenylacetate is obtained, as described in Schwenk et al. J. Am. Chem. Soc. 70, 3626 (1948), and the bromoester obtained, through reaction with ethylenediamine, leads to the obtention of the mentioned starting compound (3), as described in Roderick et al. J. Med. Chem. 9(2), 181-5 (1966).

The summarised method has several drawbacks, such as for example the need to use reagents like bromine and methyl iodine and solvents like chlorobenzene, which are highly toxic products, with the main drawback being the fact that in the final methylation stage it is very difficult to apply controls to avoid the formation of large amounts of N,N'-dimethylated compound and methylated compound in the unwanted nitrogen. This explains the low yields obtained despite working in high dissolution conditions, which introduces a further drawback in the handling of large amounts of solvent, with the consequent increase in cost, low efficiency per reaction volume and the need to recover the solvents.

The method that is the object of the invention overcomes such problems because it makes it possible to univocally obtain the correct N-methylated product by means of a simple method that does not require the use of reagents that are highly toxic and difficult to handle.

OBJECT OF THE INVENTION

The object of the invention is a method for obtaining the compound (±)-3-phenyl-1-methylpiperazine, an intermediate for preparing mirtazapine, in which the final step consists of the formation of the piperazine ring.

Also forming part of the object of the invention are new intermediate compounds whose reduction and cyclization enable the compound (±)-3-phenyl-1-methylpiperazine to be obtained directly, as well as a method for obtaining said new intermediate compounds.

DESCRIPTION OF THE INVENTION

The inventors in this case have discovered that the compound (±)-3-phenyl-1-methylpiperazine can be obtained when a compound of general formula (1)

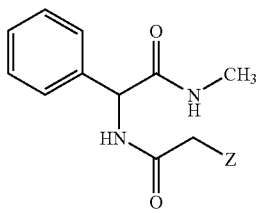

(I)

in which Z is a leaving group, undergoes a cyclization reaction in the presence of a reducing agent.

For the purposes of this invention the leaving group is understood to be a chemical group capable of undergoing a nucleonhilic displacement in the nucleophilic substitution reaction generated by the actual piperazine ring of compound (±)-3-phenyl-1-methylpiperazine. The leaving groups capable of undergoing a nucleophilic displacement are well known to the person skilled in the art, and they include, although not exclusively, the following: halogen (fluorine, chlorine, bromine, iodine); alkylsulphonyloxy, possibly substituted, (mesyloxy, triflate, . . . ) or arylsulphonyloxy, possibly substituted (besyloxy, tosyloxy, . . . ); hydroxy or alkoxy; thiol or alkylmercapto; etc.

Preferably, the reduction/cyclization reaction uses a borane as reducing agent, for example borane ($BH_3$) or the complex thereof with tetrahydrofuran (THE), or diborane ($B_2H_6$).

The bibliography contains descriptions of reduction methods which can be used to carry out the method that is the object of this invention. So, for example, in Brienne et al. Eur. J. Med. Chem. —Chimica Thereapeutica, 16(4), 363-6 (1981) describes a reduction method that uses $BH_3$.THF as the reducing agent, which is a commercially available complex consisting of borane and tetrahydrofuran, and which can also be obtained by dissolving diborane in said solvent.

U.S. Pat. No. 5,681,962, example 2, also describes a reduction method that can be used in the method that is the object of the invention, in which borane is produced "in situ" from sodium boro-hydride ($NaBH_4$) and hydrogen chloride in dimethoxyethane (DME). Alternatively, in this method, other strong mineral acids can be used instead of hydrogen chloride (hydrochloric acid), for example, sulphuric acid, or Lewis acids, with boron trifluoride ($BF_3$) being preferable in the complex thereof with ethyl ether (boron trifluoride ethyletherate) which is commercially available and can be handled comfortably without any problems.

U.S. Pat. No. 5,378,729 provides a general description of compounds that can be assigned to the general formula

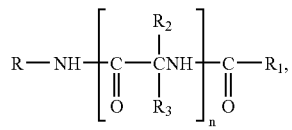

including the compounds of general formula (I), the object of the invention, when the following meanings foreseen in said patent are applied: R short chain alkyl group; $R_1$ short chain alkyl group substituted with an electron attracting group; $R_2$ hydrogen; $R_3$ phenyl; and n=1. Example 4 of U.S. Pat. No. 5,378,729 describes compound N-acetyl-D,L-phenylglycine-N'-methylamide, of formula

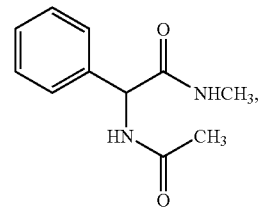

which is the closest to the compounds of general formula (I) out of those explicitly described in said patent. However, said patent does not explicitly describe any of the products that can be assigned to general formula (I).

Consequently, the compounds of general formula (I) are new and form part of the object of this invention. The preferred compounds are those in which Z is halogen, with the compound 2-chloroacetamide-N-methyl-2-phenylacetamide being particularly preferable, of formula

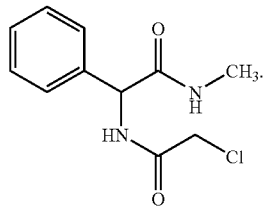

The compounds of formula (I) have a chiral centre, whereby they can appear in the form of racemic mixtures, mixtures enriched in one of the two enantiomers thereof and even in the form of any of the two pure enantiomers thereof. It must be understood that all the forms mentioned are included in the object of this invention.

The compounds of formula (I) can be prepared by means of a method based on the following synthesis diagram.

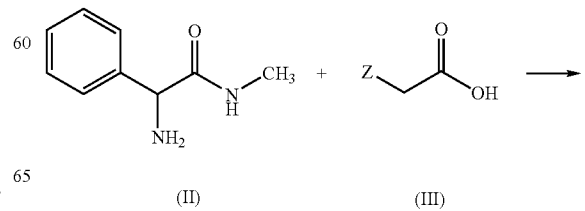

(II)        (III)

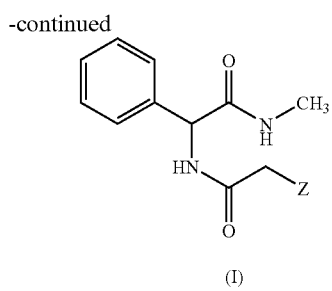

(I)

Thus, an amidation reaction is produced between 2-amino-2-phenyl-(N-methyl)acetamide (II) and acid (III), in which Z has the afore-mentioned meaning. Preferably, acid (III) is activated prior to the amidation reaction using known techniques, such as the formation of acid halides, anhydrides, mixed anhydrides, active esters, etc., or said acid (III) is used directly employing a coupling agent, such as for example dicyclohexylcarbodiimide (DCC).

Preferably, the amidation reaction of (II) is carried out through reaction with the chloride of monochloroacetic acid in the presence of a hydrochloric acid accepting base, for example sodium carbonate.

Resolving the racemic mixtures of formula (I) compounds into the enantiomers thereof can be carried out using conventional methods, well known to the person skilled in the art, such as for example chromatography techniques. The pure enantiomers can also be obtained directly by means of stereospecific synthesis.

Compound 2-amino-2-phenyl-(N-methyl)acetamide of formula (II) is known and is described in the literature, as well as methods for the obtention thereof. For example, the compound of formula (II) can be obtained by means of the methods described in the following publications:

Cortés et al. J. Med. Chem. 28, 601-606 (1985),
Feenstra et al. Tetrahedron 46(5), 1745-1756 (1990), and
Jacquier et al. Bull. Soc. Chim. France 3, 1040-1052 (1971), which are based on the following synthesis diagram:

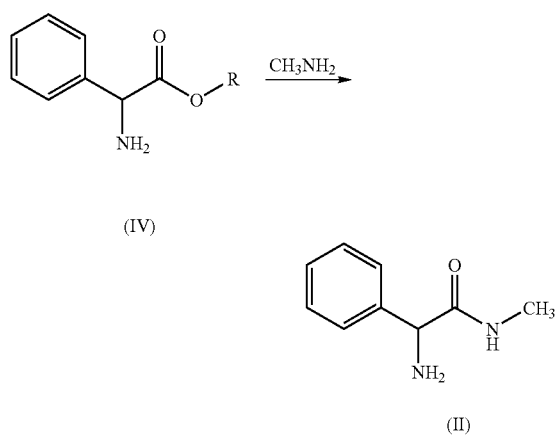

In other words, an ester, preferably methyl or ethyl, of DL-α-phenylglycine is reacted with methylamine to obtain compound (II). The esters of DL-α-phenylglycine can be obtained easily by means of general methods for obtaining amino acid esters such as, for example, that described in Akhlaq et al. J. Org. Chem. 27, 4527-45231 (1962).

The following examples are offered to provide the person skilled in the art with a sufficiently clear and complete explanation of this invention, but should not be considered as limitations to the essential aspects of the object thereof, as they have been explained in the earlier sections of this specification.

EXAMPLES

Example 1

Obtaining methyl DL-α-phenylglycinate Hydrochloride (IV)

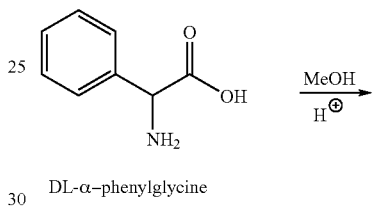

DL-α-phenylglycine

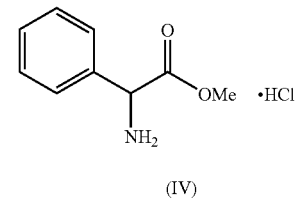

(IV)

DL-α-phenylglycine (394.7 g, 2.611 mol) and a solution of methanol/HCl 4.3 N (3940 mL, 16.942 mol) were placed in a 5 L glass reactor and the granulate suspension was stirred at room temperature (20°±2° C.) for 18 hours, with its conversion into a clear solution being observed after approximately 4 hours and its conversion into a cloudy solution (fine suspension) after 8-10 hours. The mixture was concentrated at reduced pressure to an approximate volume of 1.0 L, with approximately 3.3 L having been distilled. In this way, a thick, white suspension was obtained which was cooled to 20°±1° C. and was filtered, with the filter being washed with methanol (300 mL). The resulting solid was dried at 60° C. and atmospheric pressure to constant weight (455.8 g). The filtrate was concentrated again under reduced pressure to an approximate volume of 135 mL, with approximately 600 mL having been distilled. The thick, natural coloured suspension was cooled to 20°±1° C. and was filtered, with the filter being washed with methanol (50 mL). The resulting solid was dried at 60° C. and atmospheric pressure to constant weight (40.4 g). Both solids contained the title product (IV) (496.2 g, 94.3% yield).

$^1$H NMR (200 MHz, CD$_3$OD)δ:4.01 (s, 3 H, CH$_3$), 5.11 (s, 3 H, NH$_3^+$), 5.44 (s, 1 H, CH), 7.66 (s, 5 H, Ar—H).

Example 2

Obtaining (±)-2-amino-2-phenyl-(N-methyl)acetamide (II)

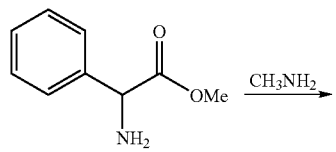

(IV)

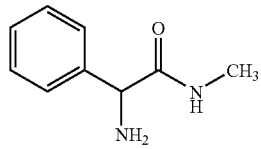

(II)

Compound (IV) of the previous example (493.0 g, 2.445 mol) and an aqueous solution of methylamine 35.5% (p/p) (1188.0 mL, 12.226 mol) were placed in a 5 L glass reactor and a slight exothermic reaction of 5°-6° C. was observed. The resulting solution was stirred at 21°±1° C. for 1.5 hours and was extracted with dichloromethane (5×986 mL and 2×493 mL) until TLC showed no presence of the desired product in the aqueous phase. The accumulated organic extracts were evaporated at reduced pressure and a thick oily residue was obtained having a yellowish colour and a slightly cloudy appearance, corresponding to the title product (II) (400 g, 99.6% yield).

$^1$H NMR (200 MHz, CD$_3$OD)δ:2.91 (s, 3 H, CH$_3$), 4.60 (s, 1 H, CH), 5.07 (s, 3 H, NH, NH$_2$), 7.48-7.61 (abs. compl., 5 H, Ar—H).

Example 3

Obtaining (±)-2-chloroacetamide-N-methyl-2-phenylacetamide (I)

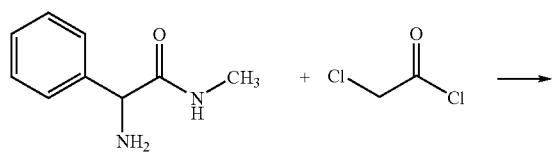

Compound (II) obtained in the previous example (395.0 g, 2.405 mol) and acetone (1074 mL) were placed in a 5 L glass reactor and deionised water (1303 mL) was added to the slightly cloudy resulting solution, with a slight exothermic reaction of 6° C. being observed. Then, Na$_2$CO$_3$ (153.0 g, 1.443 mol) was added, with a slight exothermic reaction of 2° C. being observed. The resulting whitish suspension was cooled with an ice water bath at 0°-5° C. and, for approximately 1 hour without exceeding 5° C., a solution made up of chloroacetyl chloride (III) (201.0 mL, 285.3 g, 2.526 mol) in acetone (735 mL) was slowly added. The addition created vapours and a slight release of gases. The resulting milky suspension was stirred at 0°-5° C. and, after 1.5 hours, Na$_2$CO$_3$ (30.6 g, 0.289 mol) and a solution made up of chloroacetyl chloride (38.3 mL, 54.3 g, 0.481 mol) in acetone (140 mL) was added. After a further 1.5 hours, the suspension was concentrated at reduced pressure to a volume of approximately 1.0 L, with approximately 3.0 L having been distilled. The white thick suspension was cooled to 18°±2° C. and was filtered, with the filter being washed with deionised water (300 mL). A white solid was obtained that was dried at 60° C. and at reduced pressure and, which corresponded to the title product (I), having a melting point of 192-194° C. (483.7 g, 83.55% yield).

$^1$H-NMR (300 MHz, DMSO-d$_6$)δ:2.57 (d, J=4.5 Hz, 3 H, CH$_3$), 4.18 (s, 2 H, CH$_2$Cl), 5.40 (d, J=7.8 Hz, 1 H, CH), 7.24-7.40 (abs. compl. 5 H, Ar—H), 8.33 (c, J=4.8 Hz, 1 H, NH—CH$_3$), 8.90 (d, J=8.1 Hz, 1 H, NH—CH). $^{13}$C-NMR (75.4 MHz, DMSO-d$_6$)δ:25.9 (CH$_3$, NH—CH$_3$), 42.7 (CH$_2$, CH$_2$Cl), 56.6 (CH, NH—CH), 127.8 (CH, Ar—C$_{para}$, 127.1 and 128.6 (CH, Ar—C$_{ortho}$ and Ar—C$_{meta}$), 138.7 (C, Ar—C$_{ipso}$), 165.6 and 169.8 (C, 2 CO—NH).

The product obtained has sufficient quality to be used to obtain (±)-3-phenyl-1-methylpiperazine, but if desired, for analytical purposes, it can be purified by being washed by alternative suspension in acetone and water until a product is obtained having a melting point of 194-195° C. with a purity in the region of 99.9% (HPLC).

Example 4

Obtaining (±)-3-phenyl-1-methylpiperazine

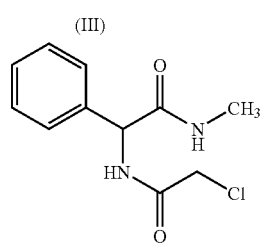
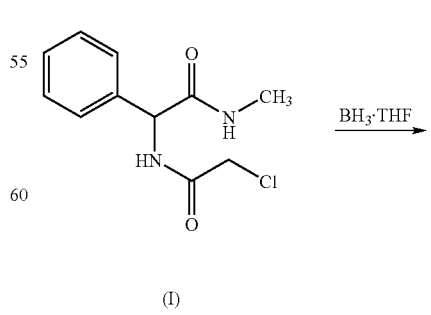

(I)

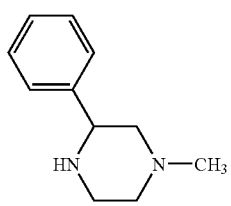

(±)-3-phenyl-1-methylpiperazine

Compound (I) of the previous example (0.5 g, 2.077 mmol) and tetrahydrofurane (5 mL) were placed in a 25 mL flask, and for approximately 10 minutes the BH$_3$.THF complex 1 M (10.4 mL, 10.386 mmol) was added to the white suspension. The resulting colourless solution was heated to reflux temperature for 6.5 hours, it was cooled to 19°±1° C. and an aqueous solution of HCl 6 N (1.82 mL) was added slowly. The mixture was distilled at reduced pressure to remove the tetrahydrofurane. Ethyl acetate (5 mL) was added and was extracted with an aqueous solution of HCl 2 N (3×5 mL). The accumulated acidic phases were alkalinised with an aqueous solution of NaOH 50% (p/p) to pH 12-13 (1.1 mL), saturated with NaCl (6.25 g) and were extracted with ethyl acetate (3×5 mL). The accumulated organic phases were dried with anhydrous Na$_2$SO$_4$, they were filtered and evaporated at reduced pressure, giving a yellowish liquid residue which corresponded to the title product (0.3 g, 81.97%).

$^1$H-NMR (300 MHz, CDCl$_3$)δ:2.05 (pseudo t, J=10.7 Hz) and 2.20 (pseudo dt, J=11.0 Hz, J'=4.4 Hz) (2H, piperazine-2H), 2.34 (s, 3 H, CH$_3$), 2.7-3.0 (abs. compl., 3 H, NH and piperazine-2H), 3.04-3.16 (abs. compl., 2 H, piperazine-2H), 3.91 (dd, J=10.2 Hz, J'=2.7 Hz, 1 H, piperazine-CH), 7.26-7.42 (abs. compl., 5 H, Ar—H). $^{13}$C NMR (75.4 MHz, CDCl$_3$)δ:46.0 (CH$_2$, C5), 46.1 (CH$_3$, N—CH$_3$), 55.0 (CH$_2$, C6), 60.1 (CH, C3), 62.9 (CH$_2$, C2), 126.9 and 128.4 (CH, Ar—C$_{ortho}$ and Ar—C$_{meta}$), 127.5 (CH, Ar—C$_{para}$, 142.0 (C, Ar—C$_{ipso}$). ME (IE, direct introduction, 70 eV), m/z (%): 176 (M$^{·+}$, 1), 118 (3), 104 (C$_8$H$_8$$^{·+}$, 12), 58 (C$_3$H$_8$N$^+$, 100).

Example 5

Obtaining (±)-3-phenyl-1-methylpiperazine

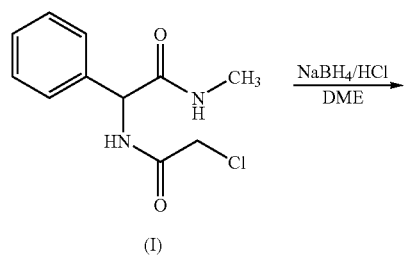

(I)

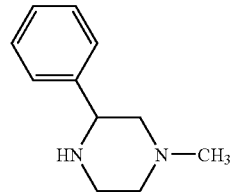

(±)-3-phenyl-1-methylpiperazine

NaBH$_4$ (75.4 g, 1.99 mol) and compound (I) obtained in example 3 (80 g, 0.332 mol) were placed in a 2 L cylindrical reactor. The mixture was cooled to 0°-50° C. with an ice water bath and 1,2-dimethoxyethane (640 mL) was loaded, with an exothermic reaction of approximately 8° C. being observed and hardly any gas release. The suspension was cooled to 0°-5° C. and a solution of 1,2-dimethoxyethane/HCl 6.5 N (297 mL, 1.93 mol) was slowly added without exceeding 20° C., with an exothermic reaction being observed and an intense gas release. The mixture was heated to 42°±30° C. for 6 hours, it was cooled to 10°-15° C. and an aqueous solution of HCl 6 N was added to pH 1 (305 mL), with an exothermic reaction being observed and an intense gas release. The resulting whitish suspension was stirred at 20°±2° C. for at least 1 hour, it was cooled to 10°-15° C.; alkalinised with an aqueous solution of NaOH 50% (p/p) to pH 12-14 (170 mL) and extracted with dichloromethane (3×250 mL). The accumulated organic phases were evaporated at reduced pressure, giving a yellowish liquid residue corresponding to the title product (56.33 g, 96.15%).

The invention claimed is:

1. Compound of general formula (I)

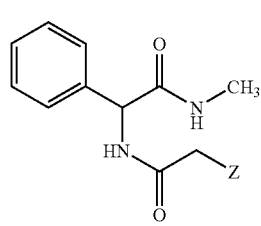

(I)

in which Z is selected from the group consisting of chlorine, alkylsulphonyloxy, arylsulphonyloxy, hydroxy, alkoxy, thiol and alkylmercapto.

2. Compound 2-chloroacetamide-N-methyl-2-phenylacetamide, of formula

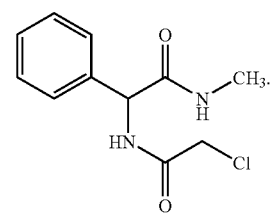

3. Method for obtaining the compound of claim 1, comprising an amidation reaction between compound 2-amino-2-phenyl-(N-methyl)acetamide, of formula (II)

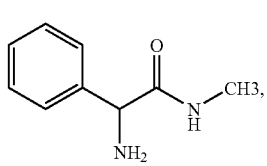

(II)

and an acid of formula (III)

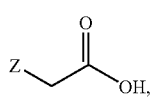

(III)

in which Z is as defined in claim 1, or with an activated derivative of said acid.

4. Method according to claim 3, wherein the activated acid derivative is selected from acid halides, anhydrides, mixed anhydrides and active esters.

5. Method according to claim 4, wherein the activated derivative is the chloride of monochloroacetic acid.

6. Method according to claim 3, wherein the amidation reaction is carried out in the presence of a base.

7. Method according to claim 6, wherein the base is sodium carbonate.

8. Method for obtaining the compound (±)-3-phenyl-1-methylpiperazine, of formula

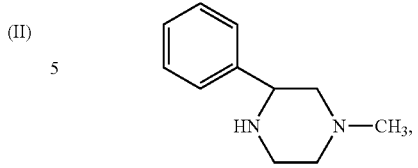

wherein a compound of general formula (I)

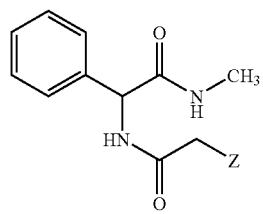

(I)

in which Z is a leaving group capable of undergoing a nucleophilic displacement undergoes a cyclization reaction in the presence of a reducing agent.

9. Method according to claim 8, wherein the reducing agent is a borane.

10. Method according to claim 9, wherein the reducing agent is borane or tetrahydrofuran $BH_3.THF$ complex.

11. Method according to claim 9, wherein the borane is prepared "in situ" from sodium boro-hydride and a strong mineral acid or a Lewis acid.

12. Method according to claim 11, wherein the strong mineral acid is hydrogen chloride in 1,2-dimethoxyethane.

13. Method according to claim 11, wherein the Lewis acid is boron trifluoride ($BF_3$) in the form of a boron trifluoride ethyletherate complex.

\* \* \* \* \*